US00PP07855P

United States Patent [19]

Jessel, Jr.

[11] Patent Number: Plant 7,855

[45] Date of Patent: Apr. 14, 1992

[54] CARNATION PLANT NAMED CFPC SUNSET

[75] Inventor: Walter H. Jessel, Jr., Salinas, Calif.

[73] Assignee: California Florida Plant Co., L.P., Salinas, Calif.

[21] Appl. No.: 580,257

[22] Filed: Sep. 10, 1990

[51] Int. Cl.[5] ..... A01H 5/00

[52] U.S. Cl. ..... Plt./70

[58] Field of Search ..... Plt./70, 73

[56] References Cited

U.S. PATENT DOCUMENTS

P.P. 6,061 12/1987 Duffett ..... Plt. 70

*Primary Examiner*—Howard J. Locker

*Attorney, Agent, or Firm*—Christie, Parker & Hale

[57] ABSTRACT

A new and unusual miniature spray carnation of orange and picotee red coloration.

1 Drawing Sheet

BACKGROUND OF THE INVENTION

Carnation varieties producing flowers of many different colors are well known. However, it is desirable to provide a new miniature variety of carnation producing sprays of flowers having orange and picotee red coloration.

SUMMARY OF THE INVENTION

The present invention relates to a new and distinct variety of carnation plant which was originated by me in a controlled breeding program by my crossing as seed and pollen parents, two numbered but unnamed and unpatented seedlings of my creation. The varietal denomination of this new carnation is 'CFPC Sunset'.

Among the novel characteristics possessed by the new variety which distinguish it from its parents and all other varieties of which I am aware are the unusual flower coloring for a carnation and early flowering response.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety in different stages of development, depicted in color as nearly true as it is reasonably possible to make the same in color illustration of this character.

DESCRIPTION OF THE NEW VARIETY

The new variety, 'CFPC Sunset', produces sprays of flowers of unusual coloring, and strong straight stems; with an average of five open flowers and buds per spray. The new variety also has a strong calyx with very little splitting. 'CFPC Sunset' exhibits early response which, together with its attractive and unusual coloring and the other characteristics heretofore and hereinafter described, make it especially suitable for commercial spray-type cut flower production.

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Sunset.

Classification:

*Botanical.*—*Dianthus caryophyllus.*

*Commercial.*—Greenhouse type, suitable for cut flower production as a spray.

Parentage:

*Female parent.*—Unnamed seedling (No. 0133).

*Male parent*—Unnamed seedling (No. 0162).

PLANT

Height: About 39 inches.

Growing habit: Herbaceous, semi-upright.

Blooming habit: Terminal as a spray.

Blooming season: Year round.

Rooting time: About 18 days.

Mutation prone: No.

Disease resistance: Unknown.

Temperature tolerance: Typical for carnation.

FOLIAGE

Color:

*Upper side.*—Near to 136B.

*Lower side.*—Near to 137A.

Size: About 5¼ inches long and about ⅜-inch wide at base of plant.

Quantity: Numerous.

Shape: Lanceolate.

Texture: Smooth.

Ribs: Central keel.

Arrangement: Bi-lateral along stem.

Stem:

*Color* —Green.

BUD

Shape: Oval.

Color: Near to 132B.

Length: About ¾ to 1 inch.

Diameter: About $\frac{2}{3}$ to $\frac{3}{4}$ inch.

CALYX

Number of lobes (sepals): About 6.
Length: About 1 inch.
Width: About $\frac{3}{4}$ inch.
Color:
*Outside.*—Near to 132B.
*Inside.*—Near to 130C.

BLOOM

Borne: Terminal as a spray.
Color:
*General tonality.*—Orange with a red picotee border on petals.
*Upper side.*—Primary or base color is from near 29C to near 28*D;* picotee edge color is from near 46B to C to 50A.
*Reverse.*—Base color is near to 28D, picotee edge color is near 50A.
*Outer petals.*—Picotee edge is near 50A.
Permanence: Yes.
Keeping habit: About 14 days.
Fragrance: Slight to none.
Size:
*Diameter.*—About $2\frac{2}{3}$ to $2\frac{3}{4}$ inches.
*Depth.*—About $1\frac{1}{4}$ inches.

PETALS

Number: About 20–22.
Outer petals:
*Length.*—About 2 inches.
*Width.*—About $1\frac{1}{8}$ inches.
Texture: Smooth.
Form: Fan shaped.
Central petals:

*Length.*—About $\frac{2}{3}$ inch.
*Width.*—About $\frac{1}{2}$ inch.
Appearance: Shiny.

REPRODUCTIVE ORGANS

Stamens:
*Number.*—About 13–14.
*Arrangement.*—Around the ovary.
Anthers:
*Number.*—About 13–14.
*Length.*—About $\frac{3}{8}$ to $\frac{1}{4}$ inch.
*Color.*—Near to 20B.
Filaments:
*Length.*—About $\frac{1}{2}$ to $\frac{2}{3}$ inch.
*Color.*—Near to 155C.
Pistil:
*Number.*—About 2.
*Length.*—About $\frac{3}{4}$ to 1 inch.
*Color.*—Style — near to 155A.
Stigma:
*Number.*—About 2.
*Color.*—White.
Fertility:
*Male.*—Yes.
*Female.*—Unknown.
Ovary:
*Shape.*—Conical, ribbed.
*Color.*—Base — greenish white. Body — greenish yellow. Apex — tan.

I claim:

1. A new and distinct variety of miniature carnation plant, substantially as shown and described, characterized particularly by flowers of attractive orange and picotee red coloration borne in sprays.

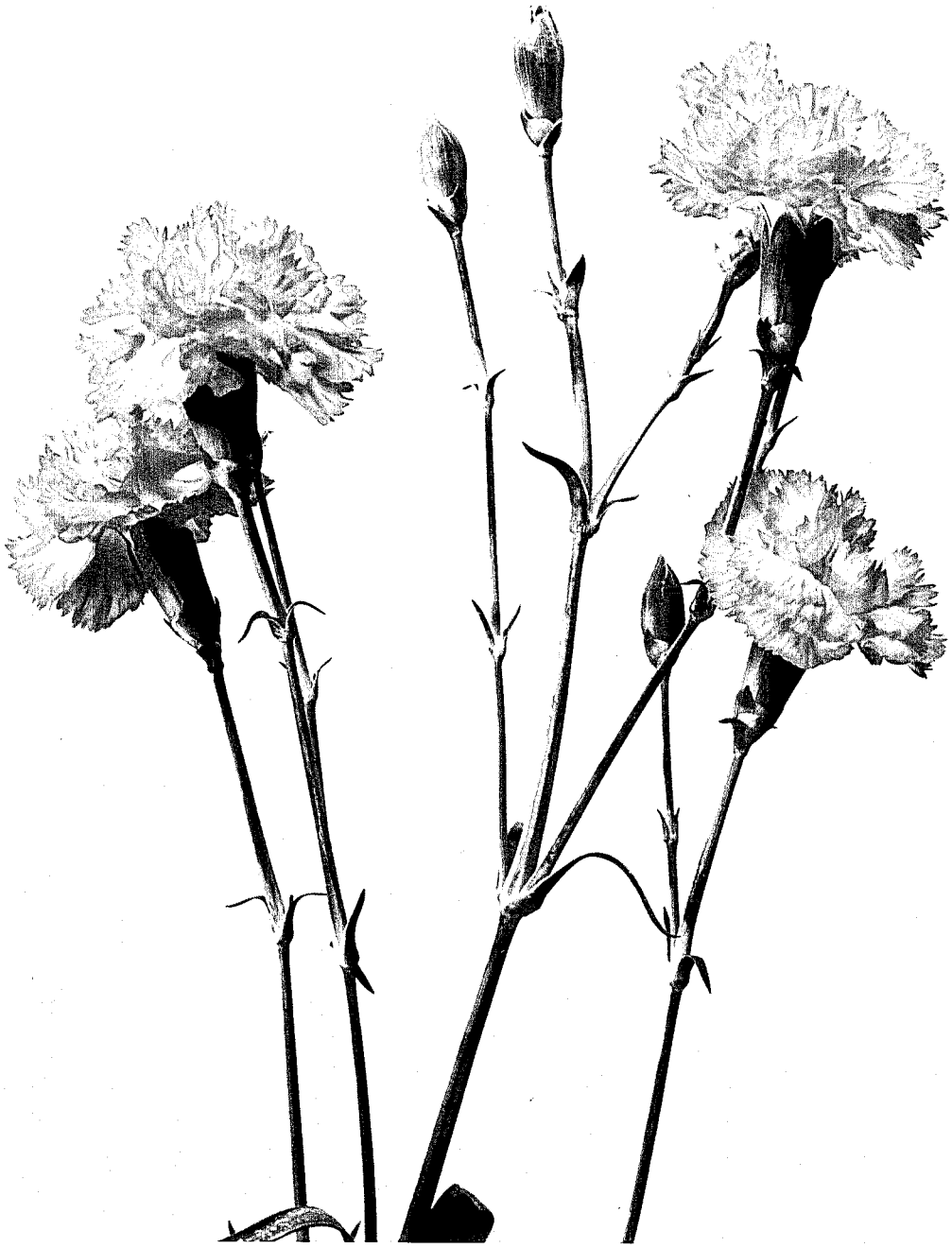

* * * * *